United States Patent [19]

Kropf

[11] Patent Number: 4,771,773
[45] Date of Patent: Sep. 20, 1988

[54] INSERTION DEVICE

[75] Inventor: Laurent Kropf, Penthaz, Switzerland

[73] Assignee: Medinvent S.A., Lausanne, Switzerland

[21] Appl. No.: 868,571

[22] Filed: May 30, 1986

[30] Foreign Application Priority Data

Jun. 10, 1985 [SE] Sweden .............................. 8502861

[51] Int. Cl.⁴ .............................................. A61B 17/00
[52] U.S. Cl. .................................. 128/303 R; 128/341
[58] Field of Search .................. 128/303 R, 341, 343, 128/334 R

[56] References Cited

U.S. PATENT DOCUMENTS 4,503,569 3/1985 Dotter .
4,553,545 11/1985 Maass et al. .................... 604/104 X
4,655,771 4/1987 Wallsten .

FOREIGN PATENT DOCUMENTS 2944133 1/1981 Fed. Rep. of Germany .

Primary Examiner—Michael H. Thaler
Attorney, Agent, or Firm—Burns, Doane, Swecker & Mathis

[57] ABSTRACT

There is provided a device for inserting an object in the form of a helical spring element with a radially variable configuration into a space which is difficult to access, particularly for medicinal use in implanting such an object in a living organism, which device includes an elongate probe, having at its insertion end a mandrel coaxial with the probe, the mandrel carrying two axially separate fasteners for the respective ends of the element, the fasteners being mutually, relatively rotatable about the axis of the mandrel for permitting the spring element to be wound tightly round the mandrel while the radial configuration of said element contracts, before insertion into the space. The fasteners are mutually connected by a transmission in the area of the mandrel. The transmission includes a freewheel which allows relative rotation for the fasteners solely in a first rotational direction for winding the spring element round the mandrel, and also includes a clutch, adapted such that on activation it allows mutual relative rotation of the fasteners, in a second opposite rotational direction. As an alternative to the clutch, one of the fasteners includes a triggering member, which is adapted such that on activation it releases the end of the spring element, tightly wound up on the mandrel, from this fastener to allow the spring element to unwind, while its radial configuration expands toward its original state. The clutch of triggering member is actuable from the end of the device remote from the mandrel.

19 Claims, 3 Drawing Sheets

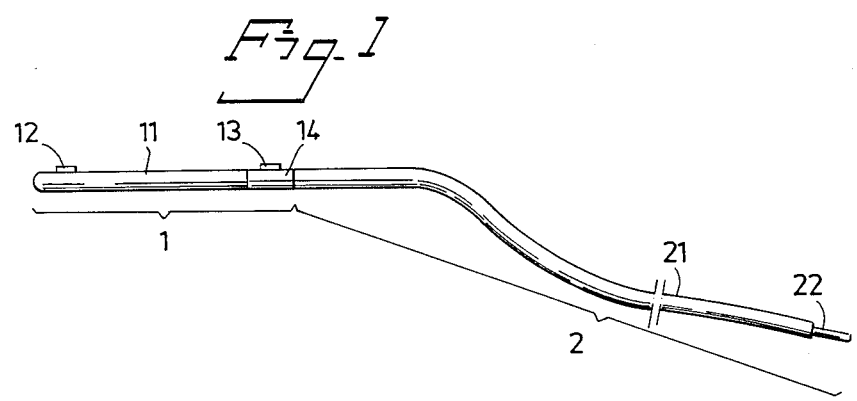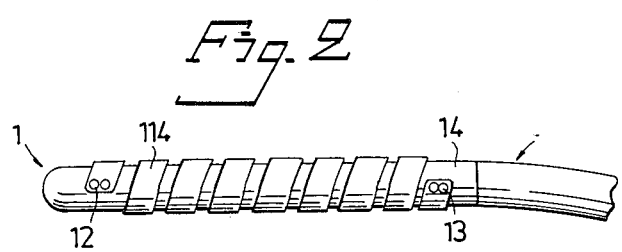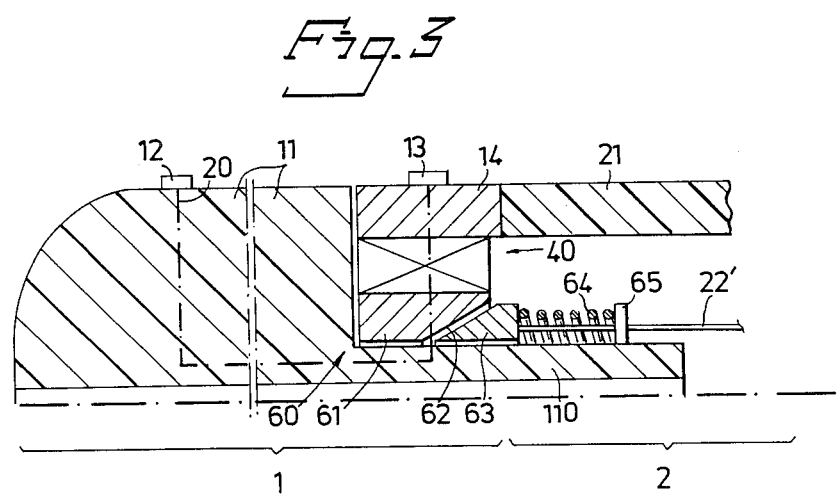

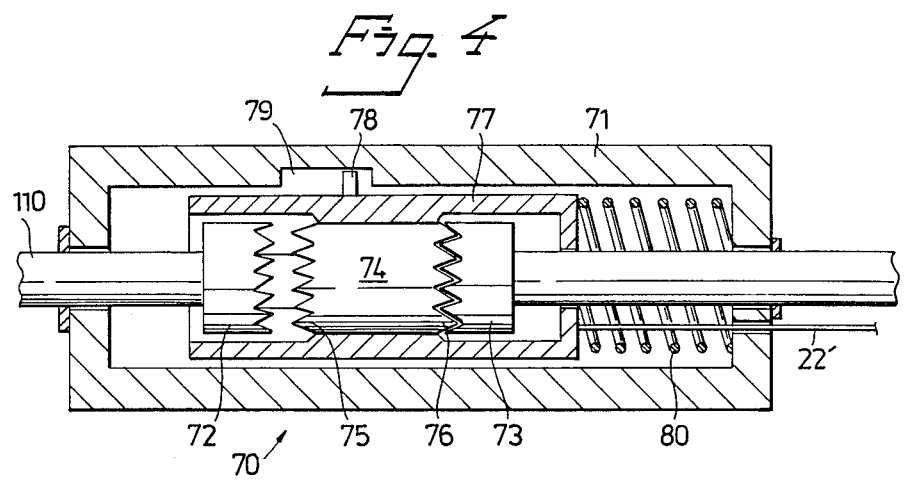
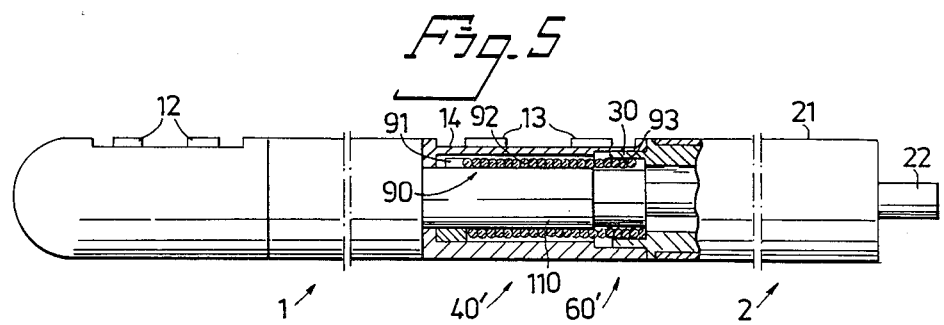
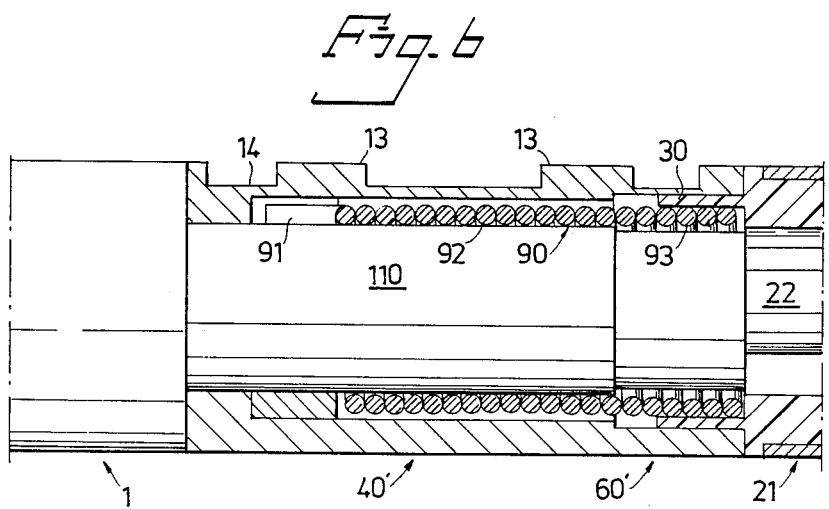

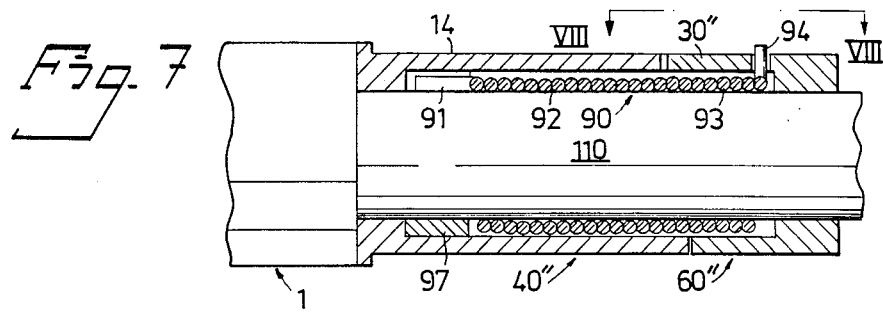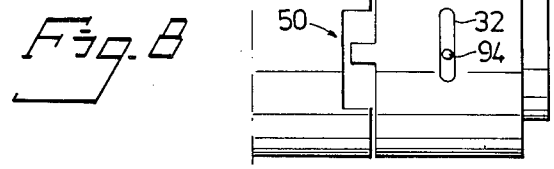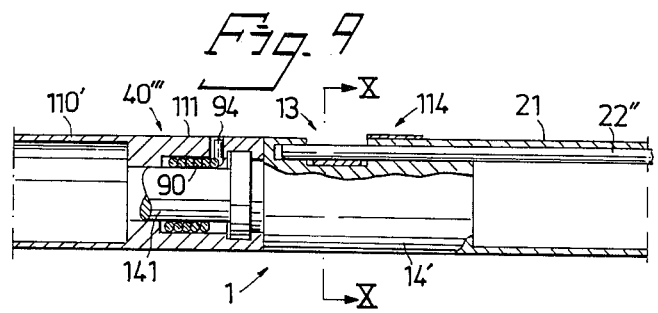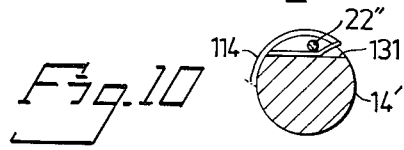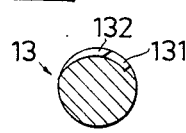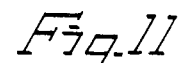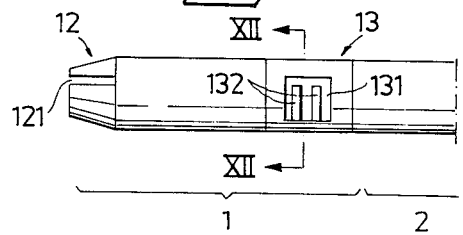

INSERTION DEVICE

TECHNICAL FIELD

The invention relates to a device for inserting an object in the form of a helical and radially elastically expandable spiral spring element into a space of difficult access, particularly for implanting such a device in a living organism, which device includes an elongate probe having at its insertion end a mandrel coaxial with the probe, said mandrel carrying two axially separate fasteners for the respective ends of the element, said fasteners being mutually, relatively rotatable about the axis of the mandrel for permitting the spring element to be wound tightly round the mandrel while the radial configuration of said element contracts before insertion into the space.

BACKGROUND ART

A so-called graft for reinforcing or replacing a wall in a hollow cavity in the body, such as an artery, vein or the like can to advantage have the form of a helix spring which, when it is released at the place of implantation, expands its radial configuration with relative turning of its ends about its axis. For enabling the insertion of the element into the intended location with the aid of the device, the latter is conventionally formed in the mannner explained above. The spring element is wound up on the mandrel, which has a diameter less than the diameter of the unbiased spring element, the ends of the latter being releasably connected to the axially separated element fasteners on the mandrel. These fasteners are mutually relatively rotatable about the mandrel axis. When the spring element is wound on to the mandrel, it strives to mutually relatively rotate the fasteners.

In order to prevent such relative rotation of the fasteners, and thus unwinding of the spring element before the mandrel with it is inserted into the intended place, the forward fastener of the mandrel is conventionally arranged to be rigidly attached to a flexible shaft, and at the rear end of the probe to constrain the shaft and probe casing against relative rotation. Since the probe, comprising casing and shaft, must be flexible and can have considerable length, e.g. 60 cm, and often has a small outside diameter, e.g. 2 mm, the shaft and probe casing will have a considerable angle of mutual torsional twist. This twist comes partly from the torque elastically exercised by the helical spring element tightly wound up on the mandrel, and partly from the further torque which the operator applies to the probe casing and shaft for ensuring engagement of the spring element against the mandrel. This twist considerably increases the difficulty of checking and controlling the stress state of the spring element, paricularly since it is difficult to decide whether the twist comes from winding the element round the mandrel or from the probe casing and shaft.

One object of the invention is therefore to provide a device of the kind mentioned, which reduces or eliminates the mentioned drawbacks.

Further objects and advantages of the invention will be apparent from the following, or will be understood by one skilled in the art. The problem solved by the invention is particularly salient when it is desired to regulate the radial expansion of the spring element with regard to size and/or rapidity, since the relative rotation of the probe casing and shaft at the rear end of the probe will be information concerning the relative rotation of both fasteners, which is difficult to interpret.

A further object of the invention is to provide a device which, apart from affording a well-controllable expansion of the spring element, also allows winding the spring element about the mandrel at the place of implantation and/or permits positive expansion of the spring element at the implantation location, e.g. when the inherent ability of the spring element to expand radially and elastically is exhausted.

CHARACTERIZATION OF INVENTION

A device is provided for inserting an object in the form of a helical and radially elastically expandable spiral spring element into a space of difficult access, particularly for implanting such an object in a living organism, which device includes an elongate probe, having at its insertion end a mandrel coaxial with the probe, said mandrel carrying two axially separate fasteners for the respective ends of the element, said fasteners being mutually, relatively rotatable about the axis of the mandrel for permitting the spring element to be wound tightly round the mandrel, while the radial configuration of said element contracts before insertion into the space. The device is characterized in that the fasteners are mutually connected by a transmission in the region of the mandrel, in that the transmission includes a freewheel which allows relative rotation for the fasteners solely in a first rotational direction for winding the spring element round the mandrel, and in that the transmission includes a clutch, adapted such that on activation, it allows mutual relative rotation of the fasteners in a second opposite rotational direction for allowing the spring element to be unwound while its radial configuration expands to its original state as the spring returns towards its unstressed state, alternatively in that one of the fasteners includes a triggering member which is adapted such that on activation it releases the end of the spring element tightly wound up on the mandrel from this fastener, to allow the spring element to unwind, while its radial configuration expands towards its original state, with the spring returning towards its unstressed state, the coupling or triggering member being actuable from the end of the device remote from the mandrel.

By arranging in the probe mandrel a rotation transmission between the fasteners, and disposing a freewheel in this transmission, the torque of the spring element wound up on the mandrel will not cause any twist of the probe portion of the device. By the inventive arrangement the probe does not need to include any flexible shaft, and this shaft may be replaced by a pulling cord or push rod for operating the clutch coupling or the triggerable fastening, torsional twist of the probe mentioned earlier being completely avoidable.

For reasons given hereinafter, or which will be understood, it is preferred to have a probe including a probe casing accommodating a flexible shaft for torque transmission, for regulating the preferred clutch. The lost motion twist of the probe is here usually essentially constant and minor (independent of the state of the spring element stress), so that the size and rapidity of the element expansion may be manually determined with good precision. The preferred clutch is intimately associated with the preferred freewheel.

The preferred freewheel is distinguished in that the mandrel includes two parts mutually relatively rotatable about the mandrel axis, each part carrying one of the fasteners, in that the freewheel includes a helical spring, which in an unbiased state is a sliding fit round a rotationally symmetric surface on one of the mandrel parts, at least along a portion of its length, and that one end of the spring is connected to the second of the mandrel parts.

The following discussion is put forward better to understand the function of the helical spring freewheel.

Let it be assumed that the freewheel spring engages with a sliding fit against a surrounding coaxial rotationally symmetrical surface on a body along a plurality of turns. Let it further be assumed that the friction between the spring and the surface is sufficiently great to allow relative rotation of the spring ends, when one end of the spring is rotated physically in one rotational direction so that the number of spring turns begins to decrease (the diameter of the spring begins to increase). The spring will then engage against the surface of the body. If said end of the spring is rotated in the second rotational direction, the entire spring will slide against the surface, since the rotation tends to decrease the spring diameter. In the latter case, the ability to transfer torque on engagement is dependent on the buckling stiffness of the spring wire.

Of course, the freewheel may also be adapted inversely so that the spring coaxially surrounds a rotationally symmetrical surface along a plurality of turns, the torque-transferring ability of the freewheel then being dependent on the tensional strength of the spring material.

The function of the freewheel may be supplemented by axial extension or compression of the spring, so that its diameter respectively decreases or increases, but, in accordance with the present invention, it is preferred to have mutual rotation of the ends of the freewheel spring, the preference also being for a spring implementation in which the spring in its unbiased state has small space between adjacent turns so that the turns have small clearance to each other when the spring positively engages with its coacting surface.

According to a preferred embodiment of the inventive device, the probe includes an elongate flexible tube coupled to the sleeve, and a flexible, rotatable shaft extending through the tube, and connected to the mandrel. Particularly, the flexible shaft may have a through duct which continues through the mandrel up to the tip of the probe for introducing a fluid to the implantation area. In the particularly preferred embodiment, the second mandrel part is a first sleeve connected to the tube via a second sleeve coaxial with the first sleeve, this second sleeve being rigidly connected to the tube. Furthermore, the second sleeve is connected to the first sleeve via a first lost rotation motion coupling, with the spring adapted to be a sliding fit on an exterior surface of said one mandrel part in an unbiased state. The other end of the spring is connected to the second sleeve via a second lost rotation motion coupling, and said end of the spring is rigidly connected to the first sleeve. The clutch is thus formed by said couplings and is actuable by relative rotation of the shaft and tube in the said second rotational direction.

It should be quite clear, however, that the clutch may be a disengaging coupling means, e.g. a conventional disengagement coupling means which may be spring-biased into engagement and on actuation, e.g. via a pulling cord, interrupt the transmission path between both fasteners.

As an alternative, the clutch may be a stepping clutch affording for each actuation a mutual rotational movement to the fasteners in the second rotational direction, through a predetermined rotational angle. An actuating element in the form of a pulling cord, a push rod or the like, then extends through the probe and is connected to the coupling for operation thereof from the end of the probe remote from the mandrel. Such a stepping clutch thus has the advantage that for each actuation it affords unwinding of the spring element through a predetermined rotational angle, so that it is simple, e.g. by counting the number of actuations, to predetermine the radial expansion state of the spring element. A further advantage is that continued operation of the stepping clutch allows radial expansion of the spring element, even after the inherent ability of the spring element to expand has been exhausted. According to a further particularly preferred embodiment of the invention, the probe includes an elongate flexible tube connected to the sleeve, and a flexible, rotatable shaft extending through the tube and connected to the mandrel. In this case the second mandrel part is a first sleeve and a second sleeve is rigidly connected to the tube and arranged coaxial with the first sleeve. In an unbiased state, a longitudinal section of the spring connecting up with said one end of the spring is a sliding fit on an exterior surface of the said one mandrel part under the first sleeve, with clearance against the inner surface of the first sleeve. The other end portion of the spring is a sliding fit in an unbiased state of the spring on the inner surface of the second sleeve and has clearance against the surface of said first mandrel part under the second sleeve. In the latter embodiment, the clutch is formed by the second sleeve and the interchange between the second sleeve and the second end portion of the spring. The clutch is actuable by rotating the tube relative the shaft.

If the probe includes a hose-like element, the actuating element for actuation of the clutch may comprise a flexible shaft, a pulling cord, or a push rod extending through the hose-like element. If the probe includes a flexible shaft, the actuating element may comprise a flexible, hose-like element substantially coaxially surrounding the flexible shaft.

The flexible shaft may have a central duct, and this duct may be in communication with an axial duct through the mandrel to allow the introduction of a fluid such as a gas or a liquid, e.g. an X-ray contrast liquid, to the implantation location.

When one fastener is triggerable according to one alternative of the clutch, the triggering means may have the distinguishing features disclosed in claim 10.

The invention, which is disclosed in the accompanying claims, will now be described in the form of an example and with reference to the accompanying drawings.

DRAWING

FIG. 1 schematically illustrates the insertion device in accordance with the invention.

FIG. 2 schematically illustrates the insertion end of the device with a helical spring element mounted thereon.

FIG. 3 schematically illustrates a section through the insertion end of a device in accordance with the invention.

FIG. 4 schematically illustrates an axial section through the insertion end of the device, further illustrating a clutch included therein.

FIG. 5 schematically illustrates a partially sectioned side view of a preferred embodiment of the invention.

FIG. 6 illustrates to a larger scale a section through an embodiment of the freewheel and coupling in the device in accordance with FIG. 5.

FIG. 7 is an axial section of a variant of the freewheel and coupling in the device in accordance with the invention.

FIG. 8 is a view taken along the line VIII—VIII in FIG. 7.

FIG. 9 schematically illustrates an alternative device in accordance with the invention.

FIG. 10 is a section taken along the line X—X in FIG. 9.

FIG. 11 schematically illustrates the fasteners of the mandrel 1, and

FIG. 12 is a section along the line XII—XII in FIG. 11.

EMBODIMENTS

FIG. 1 schematically illustrates a medicinal implantation device including an elongate narrow, flexible probe 2 connected to a coaxial mandrel 1 carrying two separate fasteners 12, 13 for the ends of a radially expandable graft in the form of a helical spring element 114 (see FIG. 2). The rear fastener 13 is carried by a sleeve 14, rotatable relative the main portion 11 of the mandrel 1. As will be seen from FIG. 3, the sleeve 14 is connected for rotation to the mandrel part 11 via a freewheel 40 and a clutch 60. It will be seen from FIG. 3 that the fasteners 12, 13 are mutually connected via a rotational transmission indicated by the chain dotted line 20 and including the forward mandrel part 11, the clutch 60, freewheel 40 and sleeve 14. The clutch 60 is actuable via an actuating element 22' extending through the probe implemented as a flexible tube 21. The tube 21 may be rigidly connected to the sleeve 14. It will be understood that the ends of the spring element 114 can be attached to the fasteners 12, 13 and that the sleeve 14 may be rotated relative the mandrel part 11 until the spring 114 comes up tight against the exterior surface of the mandrel. The freewheel 40 allows such winding of the element 114, but prevents rotation of the sleeve 14 in the opposite direction. It will be understood that the mandrel 1, with the spring element 114 wound on to it, can be inserted into the desired location with the aid of the probe 21, and that the spring element 114 can be allowed radially to expand at this place when the clutch 60 is disengaged by pulling on the element 22'. It will be understood that the probe 21 is not subjected to any torque between its ends. The clutch 60 may be a simple disengaging clutch allowing the sleeve 14 and freewheel 40 freely to rotate relative the main part 11 of the mandrel. Alternatively, the clutch 60 may be of the braking type, i.e. it may afford controllable braking friction by controlling the actuating force in the element 22'. In the example according to FIG. 3, the clutch 60 may be regarded as comprising a ring 61 carrying the freewheel 40 and being rotatable about the mandrel shaft 110. The ring 61 has a cuneiform undercut 62. A wedge 63 complimental to the undercut 62 is movable in the axial direction of the mandrel 11 and is connected to the element 22'. There is a compression spring 64 between the rear end of the wedge 63 and a shoulder 65 on the mandrel shaft 110. The spring 64 biases the wedge 63 into engagement in the undercut 62 so that the ring 61 is non-rotatably engaged with the mandrel shaft 110. The clutch 60 can be completely or partially released by withdrawing the element 22'.

A clutch means 70 is illustrated in FIG. 4, and comprises an alternative to the clutch means 60 in FIG. 3. The clutch means 70 is a stepping clutch turning the shaft 110 through a predetermined angle for each pulling action on the element 22'. If it is assumed that the spring element 114 (see FIG. 2) is tightly wound on the mandrel 11, the spring element may be stepwise expanded controllably by repetitive pulling actuation on the element 22'. With the aid of the clutch 70 the spring element 114 may also be caused to expand its radial configuration after its elastic expansion capacity has been exhausted. The coupling 70 includes an exterior housing 71 in which the shaft 110 is mounted for rotation and axially retained. The shaft 110 is provided in the housing 71 with two axially separate coaxial and mutually facing saw tooth faces 72, 73. Between the latter, there is a sleeve 74 surrounding the shaft 110 and having at either end 75 and 76 complemental teeth to the saw tooth faces 72, 73. The sleeve 74 is fixedly connected to a surrounding sleeve 77 which is axially displaceable relative the shaft 110 inside the housing 71. The sleeve 77 has a radial pin engaging in an axial groove 79 in the inner wall of the housing 71. A compression spring 80 engages against the rear end of the sleeve 77 and the rear end wall of the housing 71. The actuating element 22' is connected to the sleeve 77. The sleeve 74 has an axial length somewhat less than the distance between the tooth faces 72, 73 such that the shaft 110 is always prevented from rotating freely relative the sleeve 74, and such that in an end position of the sleeve 74 there is always a pair of saw tooth faces 73, 76 or 72, 75 passing freely over each other. The saw tooth pairs 72, 75 and 73, 76 are mutually angularly displaced by approximately half a tooth pitch. In accordance with a particularly preferred embodiment of the invention, the freewheel 40 has the form of a helical spring which is a sliding fit on the rotationally symmetrical surface of the shaft 110, along at least a part of the spring length. A clutch 60' preferably has an implementation suited to this freewheel in such a case.

FIGS. 5 and 6 illustrate an embodiment of the special freewheel 60' and the special clutch 40'. FIG. 5 illustrates the probe 2 including a flexible tube 21 with a flexible shaft 22 accommodated therein and rigidly connected to the mandrel 11. The mandrel has a shaft 110 coaxially surrounded by a sleeve 14, which carries the fastener 13 and which is rotatable relative the shaft 110. A helical spring element 90 is accommodated in an annular gap between the sleeve 14 and shaft 110. Along its forward larger part, the spring 90 is a sliding fit on the surface of the shaft 110. The forward end 91 of the spring 90 is rigidly connected to the sleeve 14. The forward end of the tube 21 has a fixed sleeve 30. The rear end portion of the spring 90 is a sliding fit against the inner surface of the sleeve 30. The forward part of the spring 90 is adapted to have clearance against the inner surface of the sleeve 14 and the rear part of the spring 90 is arranged with clearance to the outer surface of the shaft 110. In an unbiased state, the helical spring 90 has a small clearance between its turns.

On rotation of the sleeve 14 in one direction relative the mandrel shaft 110, the spring 90 accompanies the sleeve for sliding movement, while relative unwinding of the spring 90 results in that the clearance between it and the shaft 110 increases. For rotation of the sleeve 14 in the opposite direction relative the shaft 110, the forward turns of the spring are successively brought into frictional contact with the shaft 110, so that the spring element forms a fixed connection between the shaft 110 and sleeve 14. The freewheel 40 thus allows the spring element to be tightly wound up on to the mandrel 1. The clutch 60' comprises the rear end portion 93 of the spring 90, and its interaction with the inner surface of the sleeve 30. On rotating the tube 21 in said second direction, friction is developed between the rear turns of the spring 90 and the inner surface of the sleeve 30. This friction results in that the rear end turns 93 of the spring 92 are successively caught up in a winding movement tending to increase the diameter of the spring section 93, whereby positive engagement is established between the spring part 93 and the sleeve 30. For continued rotation of the tube 21 in the second direction, this radial spring expansion is propagated forwards towards the forward section 92 of the spring, so that the diameter of the spring section 92 increases and the freewheel lock caused by the elastic unwinding force (expansion of radial configuration) of the spring element is inhibited. The ring 14 and fastener 13 are thus allowed to rotate in the second direction at the implantation location. It will be understood that the engagement between the spring part 92 and shaft 110 is progressively released by turning the tube 21 so that an angle of turn between the sleeves 30 and 14 substantially inversely proportional to the braking force is obtained between the spring part 92 and shaft 110. When the angle of turn between the sleeves 14 and 30 attains a value such that the friction between the spring part 92 and shaft 110 is substantially reduced, a torque can be applied between the fasteners 12, 13 for expanding the spring element 114 after its own elastic expansion of its radial configuration has been exhausted, by relative rotation of the flexible shaft 22 and tube 21 at the rear end of the probe 2.

A further embodiment of the freewheel 40" and clutch 60" is illustrated on FIGS. 7 and 8. As with the embodiment according to FIGS. 5 and 6, the spring 90 includes a forward end portion 92, the end of which is rigidly connected to the forward end of the sleeve 14, the spring 90 being a sliding fit on the surface of the shaft 110. A sleeve 30" is rotatably mounted on the shaft 110 and surrounds the rear end part 93 of the spring 90 with clearance. The rear end 94 of the spring is directed radially outwards and engages in an elongate slot 32 in the sleeve 30". The sleeves 14 and 30" are mutually, axially contiguous and coupled by a lost rotational motion coupling 50 comprising an axial projection on one sleeve and a circumferential end recess on the sleeve 14 for receiving the projection. The tube 21 is rigidly connected to the sleeve 30" and the flexible shaft 22 is connected to the mandrel shaft 110. When the spring element is anchored at its ends to both fasteners 12, 13 the freewheel 40" allows rotation of the sleeve 14 in said first direction so that the spring element 114 is tightly wound on the mandrel¹, the sleeve 30" and tube 21 accompanying said rotation, the lost rotational motion coupling 50 eliminating excessive stresses in the spring 90. If the sleeve 14 is rotated in the opposite direction, the spring 90 engages against the shaft 110 to prevent rotation of the sleeve 14 in the second rotational direction.

If it is desired, to release the sleeve 14 for rotation in the second direction, the sleeve 30 is rotated with the aid of the tube 21 in the second direction, whereby the rear part 93 of the spring 90 accompanies the sleeve 14 by interaction between the walls of the slot 32 and the spring end 94, so that the spring begins to unwind, and the unwinding movement of the spring is propagated towards the forward end 92 of the spring, whereby the engagement between the spring 90 and shaft 110 is interrupted in a regulatable, brakable way. Excessive torque on the spring 90 in the second direction is prevented by the coupling 50. It will be understood that a torque which is applied to the rear end of the probe between the tube 21 and the flexible shaft 22 is transmitted to the fasteners 12, 13 so that the element 114 can expand its radial configuration when its own elastic radial expansion ability is exhausted. A few embodiments of the invention have been given above, but it should be clear that modifications can be made to them within the scope of the invention, particularly in connection with the embodiments according to FIGS. 5-8. In the embodiments according to FIGS. 6 and 7 the forward end of the spring 90 is shown to be axially directed and placed in an axial slot in a slotted ring 97, which is adhered to the inner surface of the sleeve 14, but many other attachment facilities are available. In FIGS. 6 and 7, the freewheel is illustrated as including a sliding fit between the outer surface of the shaft 110 and the inner surface of the forward spring part 92, when it should be clear that the spring part 92 may be adapted so that the sliding fit is between it and the inner surface of the sleeve 14, while there is clearance between the outer surface of the shaft 110 and the inner surface of the spring end 92, whereby the forward spring end 91 may be connected to the shaft 110. With reference to FIG. 6 the inner surface of the rear spring part 93 may be a sliding fit on the outer surface of the sleeve 30 and with clearance to the inner surface of the sleeve 14.

Furthermore, in accordance with said modification and with reference to FIG. 7, the rear spring part 93 may be a sliding fit against the inner surface of the sleeve 30", whereby the spring end 94 may be directed radially inwards and engage in a groove directed circumferentially in the shaft 110.

The fasteners 12, 13 are adapted to the embodiment of the ends of the spring element 114. In one embodiment, the spring element 114 may be formed by a strip of elastic material, the plane of the strip being parallel to the mandrel surface. In this case the ends of the element 114 may have radially directed throughholes and the fasteners 12, 13 have hooks engaging the ends of the strip when the element is wound in the first direction into tight engagement against the mandrel, but release the ends when the fasteners 12, 13 are mutually, relatively rotated in the opposite direction, after the inherent elastic unwinding ability of the element 114 has been exhausted, and/or the ends of the element 114 have been radially expanded away from engagement with the fasteners 12, 13.

FIG. 9 illustrates an insertion device in accordance with the invention, in which the rear fastener 13 includes a remotely controllable triggering means 22''', which allows release of the end of the element 114 tightly wound on the mandrel, such that the radial configuration of the element can expand as the element returns towards an unstressed state. The mandrel includes a rear part 14' with a shaft neck 141 and a forward part 110' which is rotatably mounted on the rear part 14'. The forward part 110' includes a tubular part 111 surrounding the neck 141. A freewheel spring 90 according to the above, is arranged with a sliding fit on the neck 141. The other end of the spring 94 is connected to the part 111. In an unbiased state, there is clearance between the spring 90 and the part 111. The rear fastener 13 includes a recess 131 in the surface of the mandrel 1. The recess 131 extends in the circumferential direction of the mandrel along a fraction of the circumference thereof. A pin 22" is axially movable and extends axially into the recess. The element end is retained in the recess between the pin 22" and the bottom of the recess 131 and is released by withdrawal of the pin 22". In the example illustrated in FIG. 10, the element 114 may be regarded as consisting of a strip, which at least at its end has a central opening in its plane, and which preferably has a row of openings along its length at the central part of its chief surface. The width of the recess 131 may then correspond to half the width of the element strip, and receive one element strip half, the pin extending through the opening in the strip as illustrated in FIG. 10. A pulling cord 22' extends through the tube 21 to allow withdrawal of the pin from the area at the rear end of the probe.

In all embodiments, the forward fastener 12 may include a slot 121, open forwards and sideways in the front end portion of the mandrel 1. The forward end portion of the spring element may then be inserted in this slot 121 and kept therein by friction and the deflection or directional change of the element 114 at the exit from the slot, i.e. at the junction from the axial direction of the slot to its circumferential direction on the mandrel.

Since the slot 121 is open forwards, the forward end of the unstressed element may be easily released from the fastener 12 by axial withdrawal of the probe.

Alternatively, the forward fastener 12 may be formed analogous with the rear fastener 13 according to FIGS. 11 and 12, and thus have the form of a hook or urging abutment 132 which engages in said opening at the rear end of the element 114. The hooks 132 are here formed to take the element end with them in one direction and allow release of the element end in the other direction. The rear fastener 13 preferably includes a recess 131 extending in the circumferential direction of the mandrel, said recess extending along a fraction of the circumference of the mandrel for receiving the rear end of the element 114. The hook or abutment 132 is preferably arranged in the recess 131 so that they lie within the cross sectional circumference of the mandrel 1.

What is claimed is:

1. Device for inserting a helical and radially elastically expandable spiral spring element into a space which is difficult to access, particularly for medicinal use in implanting the helical spring in a living organism, which device includes an elongate probe, having at an insertion end a mandrel coaxial with the probe, said mandrel carrying two axially separate fasteners for respective ends of the spring element, said fasteners being mutually, relative rotatable about the axis of the mandrel for permitting the spring element to be wound tightly round the mandrel while the radial configuration of said element contracts, before insertion into the space, wherein the fasteners are mutually connected by a transmission in the region of the mandrel, the transmission including a freewheel allowing relative rotation for the fasteners solely in a first rotational direction for winding the spring element round the mandrel, the transmission further including a clutch which, when activated, permits mutual relative rotation of the fasteners in a second opposite rotational direction for allowing the spring element to be unwound so that the radial configuration expands to an original state as the spring returns towards an unstressed state, one of the fasteners including a triggering member which, when activated, releases one of the respective ends of the spring element tightly wound up on the mandrel from said one of the fasteners to allow the spring element to unwind while said radial configuration expands towards said original state with the spring returning towards said unstressed state, the triggering member being actuable from an end of the device remote from the mandrel, the mandrel including two parts rotatable relative to each other about the axis of the mandrel, each part carrying one of the fasteners, the freewheel including a helical spring which, in an unbiased state, has a sliding fit round a rotationally symmetric surface on one of the mandrel parts at least along a portion of said surface, one end of the helical spring being connected to the second of the mandrel parts.

2. Device as claimed in claim 1, wherein the probe includes an elongate flexible tube coupled to the second of the mandrel parts.

3. Device as claimed in claim 2, wherein the triggering means includes an axially movable pin engaging in a recess in the mandrel receiving a spring element end, the pin retaining the element end and releasing the element end by axial withdrawal from the recess, the probe includes an elongate, flexible tube connected to the mandrel, and elongate, flexible actuating element extending through the tube is connected to the pin and is manually, axially actuable from the rear end of the probe.

4. Device as claimed in claim 2, wherein a flexible, rotatable shaft extends through the tube and is unrotatably connected to said first mandrel part.

5. Device as claimed in claim 2, wherein said second mandrel part is a first sleeve connected to the tube via a second sleeve coaxial with the first sleeve, the second sleeve being rigidly connected to the tube, the second sleeve being connectable to the first sleeve via a first lost rotational motion coupling, the spring, in an unbiased state, having a sliding fit round an exterior surface on said first mandrel part, the other end of the spring being connected to the second sleeve via a second lost rotational motion coupling and said one end of the spring being rigidly connected to the first sleeve.

6. Device as claimed in claim 2, wherein said second mandrel part is a first sleeve, a second sleeve, rigidly connected to the tube, is arranged coaxially with the first sleeve, a length section, joined to said one end of the spring, being in a sliding fit in an unbiased state on an exterior surface of said first mandrel part under the first sleeve, and with clearance against the interior surface of the first sleeve, and the second end portion of the spring being in a sliding fit in an unbiased state against the inner surface of the second sleeve with a clearance against the surface of the second mandrel part under the second sleeve.

7. Device as claimed in claim 1, wherein a flexible, rotatable shaft extends through the tube and is unrotatably connected to said first mandrel part.

8. Device as claimed in claim 7, wherein said second mandrel part is a first sleeve connected to the tube via a second sleeve coaxial with the first sleeve, the second sleeve being rigidly connected to the tube, the second sleeve being connectable to the first sleeve via a first lost rotational motion coupling, the spring, in an unbiased state, having a sliding fit round an exterior surface on said first mandrel part, the other end of the spring being connected to the second sleeve via a second lost rotational motion coupling and said one end of the spring being rigidly connected to the first sleeve.

9. Device as claimed in claim 7, wherein said second mandrel part is a first sleeve, a second sleeve, rigidly connected to the tube, is arranged coaxially with the first sleeve, a length section, joined to said one end of the spring, being in a sliding fit in an unbiased state on an exterior surface of said first mandrel part under the first sleeve, and with clearance against the interior surface of the first sleeve, and the second end portion of the spring being in a sliding fit in an unbiased state against the inner surface of the second sleeve with a clearance against the surface of the second mandrel part under the second sleeve.

10. Device as claimed in claim 1, wherein said second mandrel part is a first sleeve connected to the tube via a second sleeve coaxial with the first sleeve, the second sleeve being rigidly connected to the tube, the second sleeve being connectable to the first sleeve via a first lost rotational motion coupling, the spring, in an unbiased state, having a sliding fit round an exterior surface on said first mandrel part, the other end of the spring being connected to the second sleeve via a second lost rotational motion coupling and said one end of the spring being rigidly connected to the first sleeve.

11. Device as claimed in claim 1, wherein the transmission clutch is a disengaging means which interrupts relative movement between the fasteners on activation.

12. Device as claimed in claim 1, wherein the transmission clutch is a stepping clutch which, for each actuation, permits a mutual rotational movement for the fasteners in the second rotational direction through a predetermined rotational angle, an actuating element extends through the probe and is connected to the clutch for operating the clutch from the end of the probe which is remote from the mandrel.

13. Device as claimed in claim 1, wherein said second mandrel part is a first sleeve, a second sleeve, rigidly connected to the tube, is arranged coaxially with the first sleeve, a length section, joined to said one end of the spring, being in a sliding fit in an unbiased state on an exterior surface of said first mandrel part under the first sleeve, and with clearance against the interior surface of the first sleeve, and the second end portion of the spring being in a sliding fit in an unbiased state against the inner surface of the second sleeve with a clearance against the surface of the second mandrel part under the second sleeve.

14. Device as claimed in claim 1, including an actuating element extending through the probe and being connected to the clutch for operation thereof.

15. Device as claimed in claim 14, wherein the rear element fastener of the mandrel has the form of at least one hook which engages with an opening in a rear end portion of the element for urging the end portion in the first direction.

16. Device as claimed in claim 1, wherein the forward fastener of the mandrel includes a slot which is open forwardly and transversely, said slot receiving the forward end of the element, whereby the forward end of the element may be released from its fastener by axial withdrawal of the mandrel when the element has expanded into the space.

17. Device as claimed in claim 16, wherein the rear element fastener of the mandrel has the form of at least one hook which engages with an opening in a rear end portion of the element for urging the end portion in the first direction.

18. Device as claimed in claim 1, wherein the rear element fastener of the mandrel has the form of at least one hook which engages with an opening in a rear end portion of the element for urging the end portion in the first direction.

19. Device as claimed in claim 1, wherein said first part is an exterior mandrel surface and the second part is a sleeve surrounding the mandrel surface.

* * * * *